United States Patent
Cassidy (10) Patent No.: US 8,313,460 B2
(45) Date of Patent: Nov. 20, 2012

(54) DEVICES, SYSTEMS, AND METHODS FOR WARMING FLUIDS IN MULTIPLE INTRAVENOUS FLUID CONTAINERS

(75) Inventor: David E. Cassidy, Chelmsford, MA (US)

(73) Assignee: General Electric Company, Schenectady, NY (US)

( * ) Notice: Subject to any disclaimer, the term of this patent is extended or adjusted under 35 U.S.C. 154(b) by 1303 days.

(21) Appl. No.: 11/385,174

(22) Filed: Mar. 21, 2006

(65) Prior Publication Data

US 2006/0210255 A1 Sep. 21, 2006

Related U.S. Application Data

(60) Provisional application No. 60/663,789, filed on Mar. 21, 2005, provisional application No. 60/663,857, filed on Mar. 21, 2005.

(51) Int. Cl.
*A61B 18/14* (2006.01)
*A61F 7/00* (2006.01)
*A61F 7/12* (2006.01)

(52) U.S. Cl. .......... 604/113; 604/114; 607/96; 607/104; 392/470

(58) Field of Classification Search .................. 604/113, 604/114, 93.01, 27, 28, 29, 6.13; 392/470; 607/96, 104
See application file for complete search history.

(56) References Cited

U.S. PATENT DOCUMENTS

| 5,319,170 | A | 6/1994 | Cassidy ..................... 219/630 |
| 6,336,003 | B1 | 1/2002 | Mitsunaga et al. |
| 6,423,268 | B1 * | 7/2002 | King et al. ...................... 422/44 |
| 6,480,257 | B2 * | 11/2002 | Cassidy et al. ................ 392/470 |
| 6,535,689 | B2 | 3/2003 | Augustine et al. ............ 392/470 |
| 6,882,797 | B2 * | 4/2005 | Stewart et al. ................ 392/470 |
| 2003/0114795 | A1 | 6/2003 | Faries, Jr. et al. |
| 2003/0233071 | A1 | 12/2003 | Gillespie, Jr. et al. |
| 2005/0008354 | A1 | 1/2005 | Cassidy |
| 2006/0099283 | A1 | 5/2006 | Wei et al. |

* cited by examiner

*Primary Examiner* — Matthew F DeSanto
(74) *Attorney, Agent, or Firm* — Alan Taboada; Moser Taboada (57) ABSTRACT

Devices, systems and methods for controlling fluid temperatures from more than one fluid containers prior to their infusion into a human body are disclosed. The device includes a power supply source for providing power; an input/output interface for receiving fluid temperature data from thermal sensors and for transmitting duty-cycle signals to each of the fluid warming unit; a processing unit for comparing fluid temperature data with a permissible fluid temperature range, for calculating a fluid temperature differential, and for apportioning the available work cycle of the power supply source; and a controller for adjusting the duty-cycle of each fluid warming unit based on the fluid temperature differentials, so that during each work cycle all available power provided by the power supply source is delivered to only one of the fluid warming units at a time.

25 Claims, 4 Drawing Sheets

DEVICES, SYSTEMS, AND METHODS FOR WARMING FLUIDS IN MULTIPLE INTRAVENOUS FLUID CONTAINERS

CROSS REFERENCE TO RELATED APPLICATIONS

This application claims the benefit of U.S. Provisional Application No. 60/663,789, filed on Mar. 21, 2005, and U.S. Provisional Application No. 60/663,857, filed on Mar. 21, 2005 under 35 U.S.C. §119(e), the disclosures of which are incorporated by reference herein.

STATEMENT REGARDING FEDERALLY SPONSORED RESEARCH OR DEVELOPMENT

N/A

BACKGROUND OF THE INVENTION

1. Field of the Invention

Devices, systems, and methods for warming intravenous (IV) fluids are disclosed and, more particularly, devices, systems, and methods for warming IV fluids using a single power pack and controller to control the duty-cycle of more than one fluid warming unit are disclosed.

2. Description of the Related Art

When introducing fluids into the human body, e.g., intravenously, it is desirable to maintain the fluids at a temperature at or near normal body temperature. Introduction of fluids into the human body at lower temperatures may induce shock or hypothermia and can lengthen the healing process. As a result, devices have been developed to warm fluids prior to their infusion into the human body.

For example, in pending U.S. patent application Ser. No. 10/876,824 to David E. Cassidy entitled Medical Fluid Warming System, which was publishes as Publication Number 2005/008354 and which is incorporated in its entirety herein by reference, inline fluid warmers have been developed to warm fluid in the delivery line between the fluid source, i.e., the intravenous drip bag (IV), and the point of infusion. More specifically, fluid warmers have been developed to warm fluid in the delivery line itself as the fluid passes through the delivery line or, alternatively, fluid warmers have been developed to warm fluid as the fluid passes through the fluid warmer.

In the case of the latter, fluid to be infused into a human body follows a serpentine path through a heat exchanger that warms the fluid to a desired temperature. Temperature sensors at the input and output of the warming device provide fluid temperature data to a controller, e.g., a proportional-integral-derivative (PID) controller. The PID controller provides signals to control the switching ON and OFF of a gate(s). The state of the gate signal controls whether power from a power source is applied or withheld from the heat exchanger.

Because the gates are binary, they are either ON or OFF. When OFF, the power source is idle, awaiting fluid temperature data that will cause it to open the gate.

Slender poles on wheels or casters are used in medical facilities to support and/or transport one or more IVs and related, mounted ancillary equipment, e.g., fluid warming units to warm the fluid in the IVs, pumps to control the flow of the fluid into a patient, power sources, and the like. Necessarily, to provide sufficient head for the IV drip, IVs are placed uppermost on the poles, which produces a high center of gravity and imbalance. When multiple IVs are placed on a single pole, the instability is further exacerbated and may lead to overturning or tipping, which may cause injury or damage equipment.

To lower the center of gravity of the pole, related ancillary equipment, generally, can be mounted on the pole and arranged to distribute the weight of the ancillary equipment over more of the IV pole. However, the available space on a pole is still limited. Therefore, the avoidance of redundancy of ancillary equipment is desirable.

Conventionally, if a patient requires multiple IV drips that contain and deliver different medicines or fluids, because each of the different fluids may require delivery at a different rate, a fluid warming unit is dedicated to each IV to control the fluid infusion temperature. Because each fluid warming unit is provided with a unique power source, e.g., a power pack, it would be desirable to provide devices, systems, and methods to reduce the number and weight of redundant power sources by delivering power from a single power source to more than one IV fluid warming unit.

Specifically, it would be desirable to provide devices, systems, and methods that control a single power pack to operate more than one IV fluid warming unit and a controller that uses duty-cycle to control the timing of power flowing to each fluid warming unit.

More specifically, it would be desirable to provide devices, systems, and methods that sense IV fluid temperature levels; that signal fluid temperature data to the controller; and, based on fluid temperature data, that adjust the duty-cycle, e.g., by pulse width modulation (PWM), of each of the IV fluid warming units, and that, further, apportion the IV fluid warming unit duty-cycles over the work cycle of the device.

Furthermore, the location of multiple IVs, fluid warming units, and associated delivery lines on a single pole can produce a jumbled or tangled appearance, making association of a particular delivery line with its respective warming unit and/or IV difficult. Applying higher temperatures to the wrong fluids, however, could lead to serious injury.

Conventionally, colored bands have been placed on the tubing of the delivery lines. However, association of the color-tagged delivery line with its respective warming unit and/or IV is still difficult. Accordingly, it would also be desirable to provide devices, systems and methods that facilitate association of signal and/or data transmission lines that in operational association with a power pack with a particular fluid warming unit.

BRIEF SUMMARY OF THE INVENTION

A device for controlling the temperatures of plural fluids prior to their infusion into the human body is disclosed. Each of the fluid containers can be heated by a fluid warming unit that has a controllable duty-cycle.

The device includes a power source for providing power to each of the fluid warming units when the fluid warming units are ON; an input/output interface that receives fluid temperature data, e.g., from thermal sensors associated with each IV drip bag or the fluid warming unit, and that transmits duty-cycle signals to the controllers of each fluid warming unit; a processing unit for comparing fluid temperature data with a permissible fluid temperature range and for calculating a fluid temperature differential therefrom; and a controller for adjusting the duty-cycle of each fluid warming unit based on the fluid temperature differentials and on apportionment of the work cycle of the device for that duty-cycle.

In one aspect, the controller can access formulae or a look-up table that provides duty-cycle adjustments for a host of fluid temperature differentials. Preferably, during each work cycle, all available power from the power source is delivered to only one of the fluid warming units at a time.

The device also can include a display device for displaying fluid temperature data and, moreover, a gravitational sensor that can be used to orient the display on the display device so that it is readable.

The elements of the device can be housed within a front housing and a rear housing. A clamping device can be fixedly attached to either the front housing or the rear housing. The clamping device is used to releasably attach the device to a horizontally- or vertically-oriented support, e.g., an IV drip bag pole.

A system for controlling the temperatures of plural fluids prior to their infusion into the human body is also disclosed. The system includes the duty-cycle adjusting device described above; fluid warming units; and thermal sensors for providing fluid temperature data.

Also disclosed is a method for controlling the temperatures of plural fluids prior to their infusion into the human body using a single power source. The method includes providing a fluid warming unit to heat the fluids prior to their infusion into the human body; providing power to the fluid warming units during a work cycle; sampling fluid temperature in each fluid warming unit; providing fluid temperature data to a controller; and adjusting the duty-cycle of each fluid warming unit based on the fluid temperature data and on the apportionment of the power source's work cycle. Preferably, during each work cycle, only one of the fluid warming units is ON at any time and all of the available power from the power source is provided only to that ON fluid warming unit.

In one aspect of the method, adjusting the duty-cycle of the fluid warming units includes comparing fluid temperature data with permissible fluid temperature ranges; calculating a fluid temperature differential, e.g., using formulae or a lookup table; calculating a duty-cycle time for each fluid warming unit for each work cycle; apportioning the work cycle of the power source according to the duty-cycle requirements of each fluid warming unit; and transmitting duty-cycle signals to each of the fluid warming units.

BRIEF DESCRIPTION OF THE SEVERAL VIEWS OF THE DRAWINGS

The foregoing and other objects, features, and advantages of the invention will be apparent from the following more particular description of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

Figure 1:
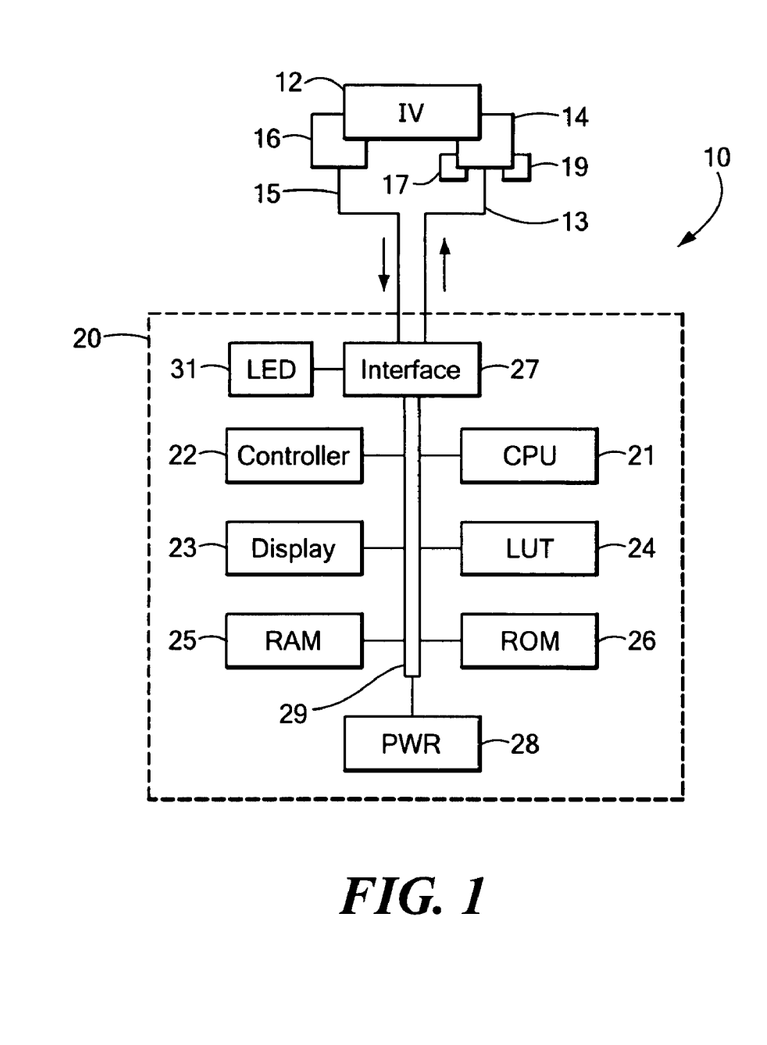
FIG. 1 provides an illustrative block diagram of a system for controlling the duty-cycle of a power pack that powers more than one IV fluid warming unit.

Referring to FIG. 1, there is shown a block diagram of a system 10 for controlling the temperature of fluids prior to their infusion into the human body. The system 10 includes a single power source, e.g. a power pack 20, for heating the fluid contained in more than one intravenous drip bag (IV) 12. Although only one IV 12 and only one power pack 20 are shown in FIG. 1, those skilled in the art can appreciate that the system 10 can include multiple IVs 12 and, if required, more than one power pack 20.

In one aspect, fluid in each IV 12 is in thermal communication with a fluid warming unit 14 and a thermal sensor 16. Although FIG. 1 depicts the fluid warming unit 14 and the thermal sensor 16 as being in direct communication with the IV 12 and, further, not in direct communication with each other, the invention is not to be construed as being limited thereto. For example, if in-line fluid warming units 14 heat the fluid within the delivery line itself, then the warming unit 14 and the thermal sensor 16 would be disposed between the IV 12 and the point of infusion, around the periphery of the delivery line. Likewise, if the fluid is heated within the in-line fluid warming units 14, then the warming unit 14 can intersect the delivery line, between the IV 12 and the point of infusion, and the thermal sensor 16 can be disposed within the fluid path of the warming unit 14.

The thermal sensor(s) 16 can be analog or digital device(s) capable of taking continuous or nearly continuous temperature measurements of the fluid in the IV 12, in the delivery line or at the input and output points of the warming unit 14.

The thermal sensor 16 converts fluid temperature measurements to fluid temperature data signals that are transmitted to the power pack 20 via a data signal line 15. The function of thermal sensors 16 is well-known to those skilled in the art, and, furthermore, described in greater detail in U.S. patent application Ser. No. 10/876,824 entitled Medical Fluid Warming System.

As described in greater detail below, the power pack 20 uses fluid temperature data from the thermal sensor(s) 16 directly or indirectly to calculate a duty-cycle for each fluid warming unit 14. Duty-cycle is the ratio of the ON time to the total cycle time during a cycle period. For example, a duty-cycle of 0.5 means that during the work cycle, the fluid warming unit 14 will be ON for one-half of the cycle and OFF for one-half of the cycle. A duty-cycle of 0.25 means that during the work cycle, the fluid warming unit 14 will be ON for one-quarter of the cycle and OFF for three-quarters of the cycle. Subsequently, the power pack 20 apportions its available work cycle time in accordance with the duty-cycle times of the fluid warming units 14.

The power pack 20 transmits PWM signals corresponding to the apportioned duty-cycle to each of the fluid warming units 14 via a signal line 13. These signals can be sent directly to the fluid warming units gates 14 to turn the gates ON or OFF or can be sent indirectly to the fluid warming unit gates via the warming unit controller (not shown).

At the beginning, e.g., t=0, and at the end of each work cycle, e.g., t=16, all fluid warming units 14 are OFF. During each work cycle, each of the fluid warming units 14 is turned ON and OFF for a variable amount of time or number of sub-cycles. This is the apportioned time of the available work cycle. In one aspect, all of the available power from the power supply source 28 in the power pack 20 is provided to the lone fluid warming unit 14 that is ON during any portion of the work cycle.

Figure 2:
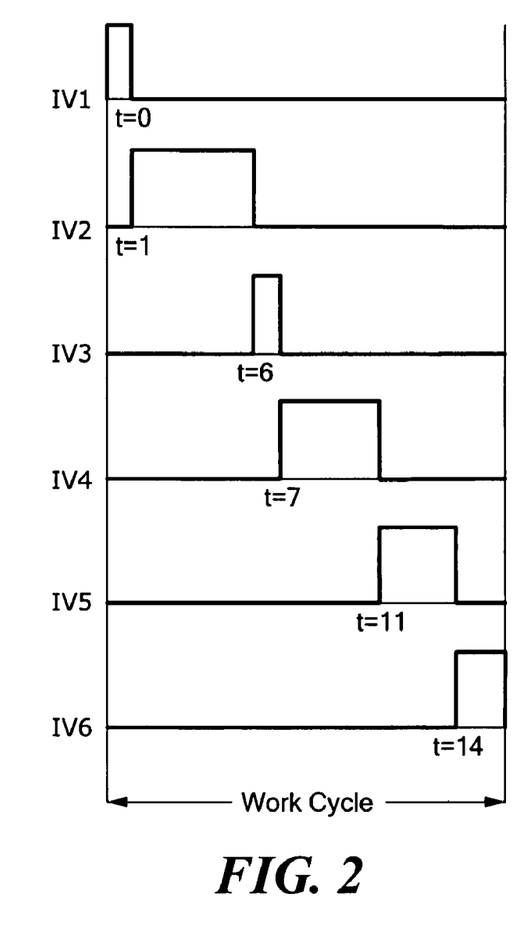
FIG. 2 provides an illustrative example of wave diagrams for six IV fluid warming units.

For example, referring to FIG. 2, there are shown illustrative wave diagrams for six IVs 12 (designated IV1 to IV6) for a work cycle. For illustrative purposes only, the work cycle shown in FIG. 2 consists of 16 sub-cycles. Each fluid warming unit 14 is ON when the voltage is high and OFF when the voltage is low. Assuming that, based on fluid temperature data signals received from the thermal sensors 16 and temperature differentials between the measured fluid temperatures and a permissible fluid temperature range, IV2 requires more heat than IV4, which requires more heat than IV5, which requires more heat than IV6, which requires more heat than IV1 or IV3, then the wave diagrams in FIG. 2 show a possible apportionment and distribution of the available power from the power supply source 28 of the single power pack 20 to all six fluid warming units 14.

Having described a system 10 for controlling the temperature of fluids prior to their infusion into the human body, the power pack device 20 there for will be described in greater detail. The power pack 20 includes a central processing unit (CPU) 21, a controller 22, a display device 23, random access memory (RAM) 25, read-only memory (ROM) 26, an input/output interface 27, a warming unit identification device 31, and a power supply source 28. The power supply source 28, e.g., a DC battery or a connection from a DC outlet, provides internal power to each of the components of the power pack 20 and, moreover, provides power to operate the fluid warming units 14 and the thermal sensors 16. An inverter (not shown) to convert AC power to DC power may be employed.

The input/output interface 27 provides one or more communication ports for connecting the power pack 20 to the fluid warming unit 14 and the thermal sensor 16 of each IV 12. Although not shown, an analog/digital converter or a digital/analog converter may also be included to convert the fluid temperature data signals from analog to digital and/or from digital to analog. Optionally, the input/output interface 27 can provide a communication port for connecting the power pack 20 to an external device, e.g., an input/output device (not shown) of an external computer (not shown). External connections allow users to program the power pack 20; to view data remotely; to run external software or hardware programs; and the like.

To facilitate association of a power pack 20 and, more specifically, the signal lines 13 and 15 connected to the power pack 20, with the respective fluid warming unit 14, a warming unit identification device 31 can be structured and arranged at the input/output interface 27 to be in operational association with the communication ports of the respective signal lines 13 and 15 and, therefore, with the respective fluid warming units 14.

At or near each of the input/output interface 27 communication ports connecting a particular warming unit 14 to the power pack 20, the identification device 31 can include an activation device (not shown), e.g., a push-button, a switch, and the like, and a visual identification device (not shown), e.g., a light-emitting diode (LED) with a discrete color. The particular warming unit 14 is also provided with a visual identification device 17, e.g., an LED with the same color as the LED on the power pack 20, as well as an audio identification device 19.

By activating the activation device associated with a particular warming unit 14, the LED on the power pack 20 associated with that activation device will light up. Simultaneously, the LED 17 on the warming unit 14, which will have the same color as the lit LED on the power pack 20, associated with the communication port will also light up and the audio identification device 19 on the warming unit 14 will emit audible signals. As a result, association of the signal lines 13 and 15 with their respective warming unit 14 is greatly simplified.

Fluid temperature data from the thermal sensors 16 are transmitted through the input/output interface 27 via a data bus 29. These data can be transmitted directly from the thermal sensors 16 or indirectly from the thermal sensors 16 via the fluid warming unit controller. Each of the central processing unit (CPU) 21, the controller 22, the display device 23, the random access memory (RAM) 25, and the read-only memory (ROM) 26 are also in communication with the data bus 29, allowing data to travel thereto, therefrom, and therebetween. Those skilled in the art are familiar with CPUs 21, display devices 23, RAM 25, ROM 26, so no discussion about these components beyond that which is necessary to describe the flow of data through the power pack 20 will be provided. Those skilled in the art can also appreciate that all or less than all of these components can be provided on a single integrated circuit chip.

After the power pack 20 receives fluid temperature data from each of the thermal sensors 16 from each of the warming units 14, each datum is compared with an optimal fluid temperature and/or a permissible fluid temperature range for the fluid. If the measured fluid temperature is within the permissible temperature range, then signals will be transmitted to the CPU 21 indicating that the fluid warming unit 14 associated with that particular warming unit 14 or IV 12 will receive a duty-cycle of zero or some de minimis amount. Hence, the fluid warming unit 14 will not be turned ON or will only be turned ON for a minimal length of time. Although it has been described that fluid temperature data are compared with permissible temperature ranges by the CPU 21, the invention is not to be construed as being limited thereto. Indeed, this comparison can also be performed by the individual controllers associated with each of the warming units 14 and the results of the comparisons transmitted to the power pack 20 instead.

On the other hand, if the measured fluid temperature falls outside of the permissible fluid temperature range, whether too high or too low, then temperature differential signals for each IV 12 or warming unit 14 will be transmitted to the CPU 21. Temperature differential signals include the temperature difference (in degrees) between the measured and the permissible fluid temperatures. How the data are used has been described in greater detail in U.S. patent application Ser. No. 10/876,824 entitled Medical Fluid Warming System and will not be discussed herein.

The CPU 21 uses the temperature differential data to estimate the desirable duty-cycle for each fluid warming unit 14. More specifically, based on the comparative needs of the fluid warming unit 14, the CPU 21 apportions the available work cycle time of the power pack 20 to satisfy the heating requirements of each of the fluid warming units 14.

For example, this can be accomplished by calling and executing an application, or program, that is stored in ROM 26, on external software and/or on external hardware. The application can allocate work cycle time based on the number of IVs 12 or fluid warming units 14 whose fluid temperature falls outside of the permissible fluid temperature range; the comparative magnitudes of the temperature differential data for each fluid; the criticality of maintaining one particular fluid within its permissible fluid range over another fluid; the volume of the fluid in the IV 12 or the fluid warming unit 14; and so forth.

In one aspect, the application accesses formulae and/or one or more look-up tables (LUT) 24 that apportion work cycle time for any possible combination of individual needs based on fluid criticality, remaining volume, and the like. The look-up table(s) 24 can be in direct communication with the CPU 21 or can also be in communication with the data bus 29. The formulae can be stored in ROM 26.

Having calculated duty-cycles for each fluid warming unit 14 and apportioned the available work cycle time of the power pack 20 to the various fluid warming units 14, the CPU 21 sends duty-cycle signals to the controller 22. The controller 22 either transmits ON/OFF signals directly to the switches (not shown) associated with each of the fluid warming units 14 or, alternatively, the controller 22 either transmits ON/OFF signals indirectly to the switches via the controller of each of the fluid warming units 14.

The signals, whether direct or indirect, open or close the switches or gates (hereinafter referred to collectively as "gates") during each work cycle according to the apportioned duty-cycle. When a specific gate is open, or ON, all available power from the power supply source 28 is delivered to that particular fluid warming unit 14.

For example, referring again to FIG. 2, at time t=0, the controller 22 sends gating signals to open the gate to IV1, keeping all other gates closed. As a result, all available power from the power supply source 28 of the power pack 20 is delivered to IV1 for one sub-cycle. At time t=1, the controller 22 send gating signals to close the gate to IV1 and to open the gate to IV2, keeping all other gates closed. As a result, all available power from the power supply source 28 of the power pack 20 is delivered to IV2 for five sub-cycles. At time t=6, the controller 22 sends gating signals to close the gate to IV2 and to open the gate to IV3, keeping all other gates closed. As a result, all available power from the power supply source 28 of the power pack 20 is now delivered to IV3 for one sub-cycle, and so forth on to IV6, when the next time cycle begins. Here again, the gating signals from the controller 22 can be direct or indirect signals.

Figure 3:
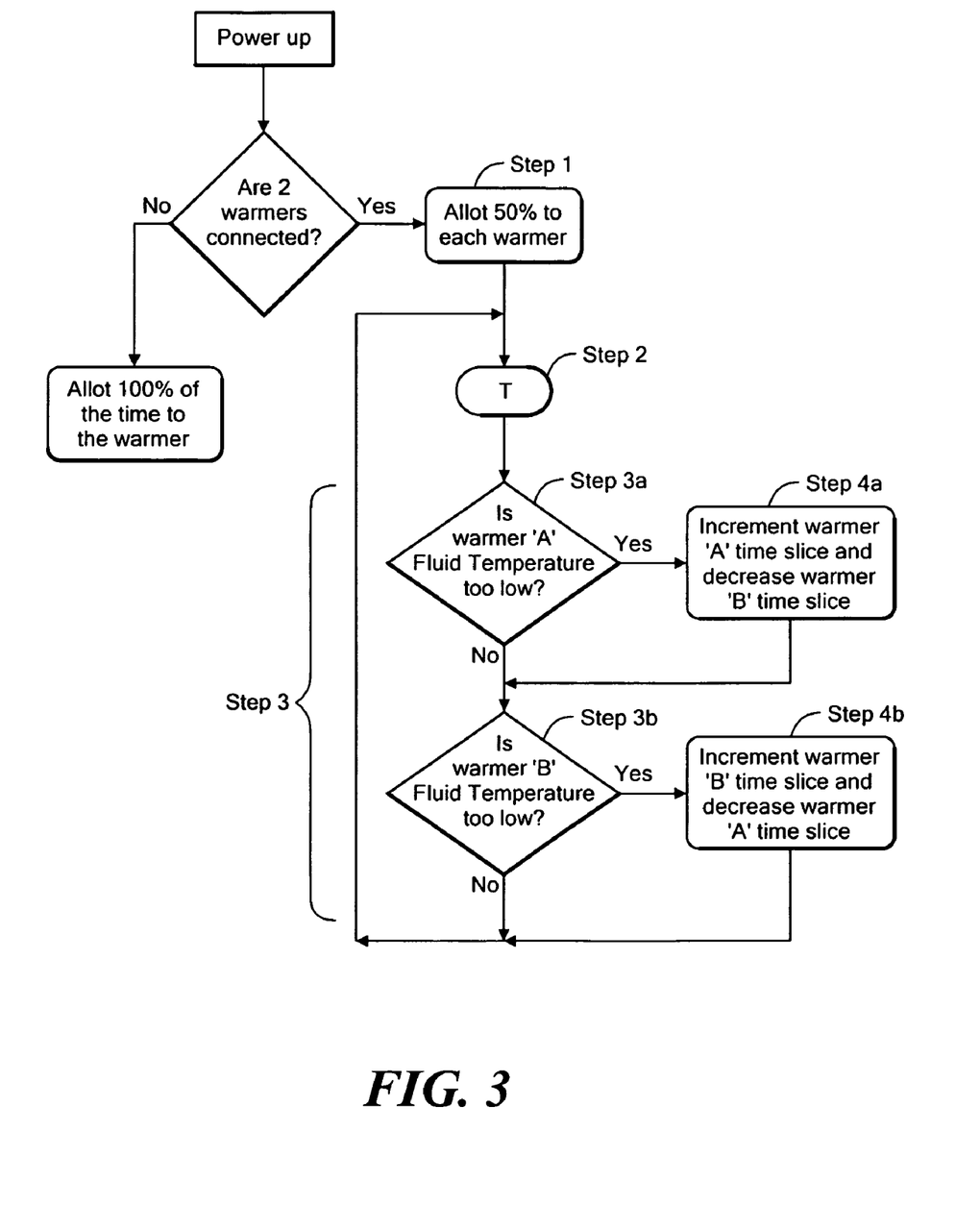
FIG. 3 provides a flow diagram of a method for controlling the duty-cycle of a power pack to two IV fluid warming units.

Having described a system and device for controlling the work cycle of a power pack 20 to power more than one IV fluid warming units 14, a method of controlling the temperature of fluids prior to their infusion into the human body is described. Referring to FIG. 3, there is shown a flow diagram for an illustrative method. Once the power pack 20 has been powered up, the CPU 21 can determine whether or not the power pack 20 is connected to a single fluid warming unit 14 or to multiple fluid warming units 14. In one aspect, the CPU 21 determines the number of fluid warming units 14 to which it is connected using fluid temperature data it receives from the thermal sensor(s) 16. If only a single fluid warming unit 14 is detected, then all available power from the power pack 20 is apportioned to the fluid warming unit 14 as needed.

If, on the other hand, multiple fluid warming units 14 are detected, then, initially, the power pack 20 determines the number (N) of fluid warming units 14 and apportions a duty-cycle of 1/N to each fluid warming unit 14 during the first work cycle (STEP 1). As the fluid warming units 14 heat the fluid in the IVs 12 or in the fluid warming units 14, fluid temperature measurements are sampled continuously by the thermal sensors (STEP 2) and fluid temperature data are transmitted to the power pack 20.

In a third step, each of the fluid temperature measurements is compared with an optimal fluid temperature and/or a permissible fluid temperature range (STEPS 3A and 3B). The optimal fluid temperature and/or fluid permissible temperature range can be digitized and stored in memory, e.g., the ROM 26. If the fluid temperature in any of the IVs 12 or fluid warming units 14 falls outside of the permissible temperature range, then proportional adjustments to the initial or previous duty-cycle are effected. For example, if the temperature of fluid A is lower than the permissible fluid temperature range for fluid A, then a temperature differential signal indicating that need for fluid A is transmitted to the CPU 21 (STEP 4A). Similarly, if the temperature of fluid B is lower than the permissible fluid temperature range for fluid B, then a temperature differential signal indicating that need for fluid B is transmitted to the CPU 21 (STEP 4B).

The CPU 21 uses temperature differential data to estimate the duty-cycle needed for each IV 12 and/or fluid warming unit 14. More specifically, the CPU 21 uses the temperature differential data to apportion the available work cycle time of the power pack 20 to each of the fluid warming units 14. This allocation of the work cycle can be done using formulae and/or a look-up table 24, (STEP 5).

In one aspect, in apportioning the work cycle time (STEP 5), in addition to the temperature differential, the CPU 21 can also take into account the magnitude of the deviation from the permissible fluid temperature range, the criticality of maintaining one fluid within its permissible fluid temperature range with respect to the criticality of maintaining another fluid within its permissible fluid temperature range, the efficiency of the fluid warming units 21, the fluid volume in each IV 12 or fluid warming unit 14, and the like.

Finally, the controller 22 transmits gating signals to open or close the gates to turn ON or turn OFF, respectively, each of the fluid warming unit switches so that only one fluid warming unit 14 is ON at any time during a work cycle. Consequently, all available power from the power supply source 28 of the power pack 20 is delivered to the lone fluid warming unit that is ON (STEP 6). Immediately after or just before each fluid warming unit 14 is turned OFF, the thermal sensors 16 provide new fluid temperature data (STEP 2) to the power pack 20 and the process continues until the fluids in all N IVs 12 or all N warming units 14 are within their permissible fluid temperature ranges and the apportioned work cycle time for each fluid warming unit 14 is about 1/N.

Figure 4:
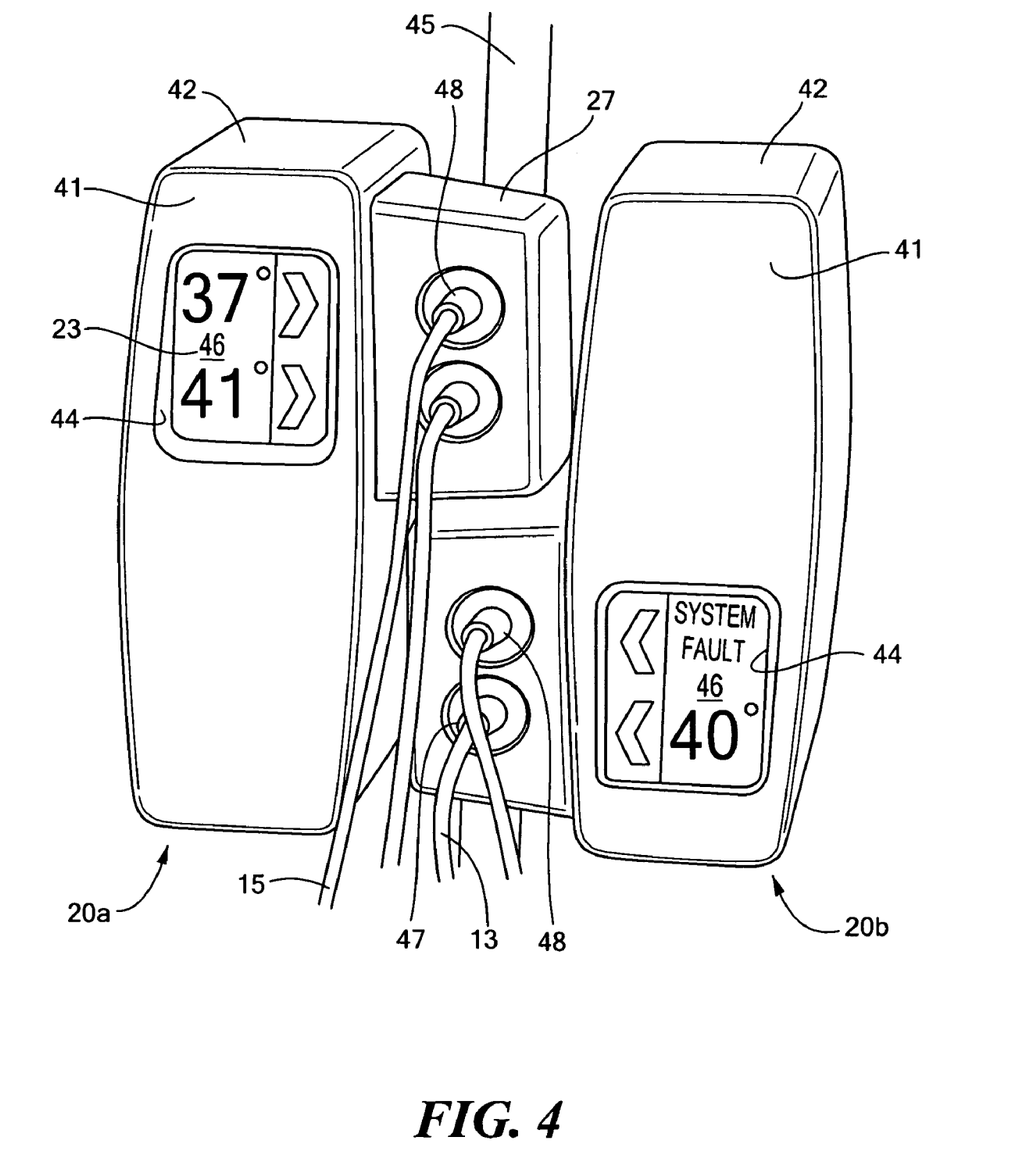
FIG. 4 provides an illustrative example of two power packs mounted adjacent to each other on a vertical IV drip bag pole.

Referring to FIG. 4, power pack devices 20a and 20b for controlling the delivery of power to more than one IV fluid warming units 14 will be described. The power pack devices 20a and 20b include a front housing 41 and a rear housing 42 that house and protect the components of the devices 20a and 20b. The front housing 41 and rear housing 42 are structured and arranged to fit together either by a tight interference fit or by using securing devices (not shown), e.g., screws, bolts, clamps, and the like. Although the adjectives "front" and "rear" will be used to differentiate between the two housing portions that encase the inner workings of the power pack 20, the housing portions could be "upper" and "lower" or "left" and "right" and/or there can be more than two portions.

The front housing 41 includes an opening 44 through which a display device 23 is visible. The display device 23 can be a liquid crystal display (LCD) device, a light-emitting diode (LED) device, an organic electro-luminous device (OEL), and the like. Preferably, a transparent, protective cover 46 to protect the display device 23 from moisture, dust, direct sunlight, shock, and the like is also included. The display device 23 and/or the protective cover 46 can be integrated into either the front housing 41 or the rear housing 42.

In one aspect of the device 20a and 20b, the input/output interface 27 is structured and arranged to be fixedly attached to either the front housing 41 or the back housing 42. The interface 27 includes plural communication ports 46 and 47 for providing communication with external devices. For example, the fluid temperature data signal line 15 can be connected to an input communication port 46 and the fluid warming unit signal line 13 can be connected to an output communication port 47. Although only two communication ports 46 and 47 are shown in communication with each of the power packs 20a and 20b, further communication ports for other external device, e.g., an I/O device to an external computer, and/or to an external power source can be included.

Figure 5:
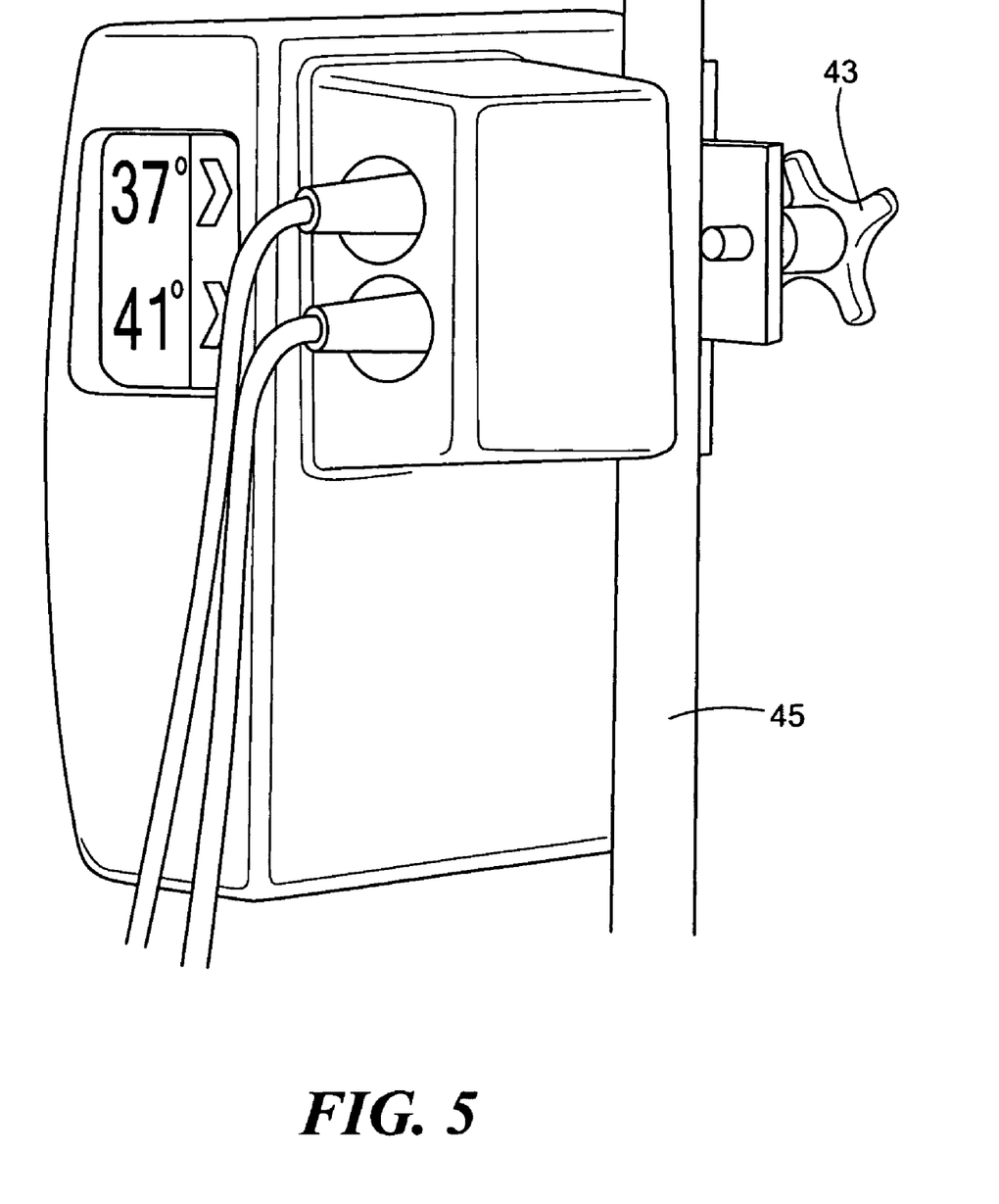
FIG. 5 provides a view of a clamping device for releasably attaching the power pack to an IV drip bag pole.

Referring to FIG. 5, each power pack 20 can include a clamping device 43 for releasably attaching the power pack 20 to an IV pole 45 that can be oriented horizontally or vertically. Although, the clamping device 43 shown in FIG. 5 is of a screw-type nature, this is done for illustratively purposes only. Those of ordinary skill in the art can appreciate the myriad of feasible clamping devices 43 that can be structured and arranged on the power pack 20.

Advantageously, each of the power packs 20a and 20b includes a gravitational sensor (not shown) to determine the orientation of the power packs 20a and 20b. The gravitational sensors provide orientation data to the CPU 21, which can be used to orient display information on the display devices 23 so that it is always readable. Accordingly, the display devices 23 are easily readable even if the power packs 20a and 20b are attached to the poles 45 up-side down, horizontally right-side up or horizontally up-side down.

Many changes in the details, materials, and arrangement of parts and steps, herein described and illustrated, can be made by those skilled in the art in light of teachings contained hereinabove. Accordingly, it will be understood that the following claims are not to be limited to the embodiments disclosed herein and can include practices other than those specifically described, and are to be interpreted as broadly as allowed under the law.

What is claimed is:

1. A device for controlling fluid temperatures from more than one fluid containers prior to their infusion into a human body, each of more than one fluids being heated by a fluid warming unit with a controllable duty-cycle, the device comprising:
 a power supply source to provide power to a plurality of fluid warming units;
 an input/output interface to receive fluid temperature data with respect to each fluid warming unit and to transmit duty-cycle signals to each fluid warming unit;
 a processing unit to compare fluid temperature data with a permissible fluid temperature range and calculate a fluid temperature differential therefrom; and
 a controller to adjust the duty-cycle of each fluid warming unit based on the fluid temperature differentials, so that during each work cycle all available power from the power supply source is delivered to only one of the fluid warming units, when both fluid warming units are on and being used at the same time.

2. The device as recited in claim 1, the device further comprising a display device for displaying fluid temperature data.

3. The device as recited in claim 2, the device further comprising a gravitational sensor that provides a gravitational orientation, which the processing unit uses to orient a display on the display device so that it is readable.

4. The device as recited in claim 1, the device further comprising
 a first housing portion and a second housing portion for housing and protecting the power supply source, the input/output interface, the processing unit, and the controller; and
 a clamping device that is fixedly attached to one of the first housing portion and the second housing portion for releasably attaching the device to a support.

5. The device as recited in claim 4, wherein the support is an intravenous drip bag pole that is oriented horizontally or vertically.

6. The device as recited in claim 1, wherein the device includes a fluid warming unit identification device that comprises an activation device and a visual identification device having a matching color to a visual identification device disposed on the respective fluid warming unit.

7. The device as recited in claim 6, wherein the activation device on the fluid warming unit identification device is further structured and arranged to provide a signal to an audio identification device disposed on the respective fluid warming unit such that, when the activation device is activated, the audio identification device emits an audible signal.

8. The device as recited in claim 1, wherein each of the more than one fluid containers is an intravenous drip bag.

9. The device as recited in claim 1, wherein the input/output interface receives fluid temperature data from a thermal sensor in association with each of the more than one fluid containers or each of the fluid warming units.

10. The device as recited in claim 1, wherein the controller can access formulae or a look-up table that provides duty-cycle adjustments for a multiplicity of fluid temperature differentials.

11. The device as recited in claim 1, wherein the processing unit apportions the work cycle of the power supply source so that the duty-cycle of each fluid warming unit is accomplished during the work cycle.

12. A system for controlling fluid temperatures from more than one fluid containers prior to their infusion into a human body, the system comprising:
 more than one fluid warming units, each having a controllable duty-cycle, each of which is associated with a respective one of the more than one fluid containers to heat fluid from the more than one fluid containers prior to infusion into the human body;
 more than one thermal sensors, each of which is associated with a respective one of the more than one fluid warming units, to provide fluid temperature data; and
 a device to adjust the duty-cycle of each fluid warming unit, the device including:
 a power supply source to provide power to the more than one fluid warming units;
 an input/output interface to receive fluid temperature data from each of the thermal sensors and to transmit duty-cycle signals to each of the more than one fluid warming units;
 a processing unit to compare fluid temperature data with a permissible fluid temperature range and calculate a fluid temperature differential therefrom; and
 a controller to adjust the duty-cycle of each fluid warming unit based on the fluid temperature differentials, so that during each work cycle all available power provided by the power supply source is delivered to only one of the fluid warming units, when both fluid warming units are on and being used at the same time.

13. The system as recited in claim 12, the device further comprising a display device for displaying fluid temperature data.

14. The system as recited in claim 13, the device further comprising a gravitational sensor that provides a gravitational orientation, which the processing unit uses to orient a display on the display device so that it is readable.

15. The system as recited in claim 12, the device further comprising:
 a first housing portion and a second housing portion for housing and protecting the power supply source, the input/output interface, the processing unit, and the controller; and
 a clamping device that is fixedly attached to one of the first housing portion and the second housing portion for releasably attaching the device to a support.

16. The system as recited in claim 15, wherein the support is an intravenous drip bag pole that is oriented horizontally or vertically.

17. The system as recited in claim 12, wherein the device for adjusting the duty-cycle of each fluid warming unit includes a fluid warming unit identification device that comprises an activation device and a visual identification device having a matching color to a visual identification device disposed on the respective fluid warming unit.

18. The device as recited in claim 17, wherein the activation device on the fluid warming unit identification device is further structured and arranged to provide a signal to an audio identification device disposed on the respective fluid warming unit such that, when the activation device is activated, the audio identification device emits an audible signal.

19. The system as recited in claim 12, wherein each of the more than one fluid containers is an intravenous drip bag.

20. The system as recited in claim 12, wherein the controller can access formulae or a look-up table that provides duty-cycle adjustments for a multiplicity of fluid temperature differentials.

21. The system as recited in claim 12, wherein the processing unit apportions the work cycle of the power supply source so that the duty-cycle of each fluid warming unit is accomplished during the work cycle.

22. A method for controlling fluid temperatures from more than one fluid containers prior to their infusion into a human body, the method comprising:
   providing a plurality of fluid warming units, each having a controllable duty-cycle, to heat a fluid from the more than one fluid containers;
   providing power from a single power supply source to each of the plurality of fluid warming units during a work cycle;
   providing a thermal sensor to sample a fluid temperature in each of the plurality of fluid warming units;
   providing fluid temperature data to a controller; and
   adjusting the duty-cycle of each fluid warming unit based on the fluid temperature data, so that, during each work cycle, available power from the single power supply source is provided to only one of the fluid warming units at a time.

23. The method as recited in claim 22, wherein adjusting the duty-cycle of each fluid warming unit includes:
   comparing fluid temperature data with a permissible fluid temperature range;
   calculating a fluid temperature differential therefrom;
   calculating a duty-cycle time for each of the plurality of fluid warming unit for each work cycle; and
   transmitting duty-cycle signals to each of the plurality of fluid warming units.

24. The method as recited in claim 23, wherein calculating a duty-cycle time for each fluid warming unit includes using formulae or a look-up table that provides duty-cycle adjustments for a multiplicity of fluid temperature differentials.

25. The method as recited in claim 23, wherein calculating the duty-cycle time for each of the plurality of fluid warming units includes apportioning the work cycle of the power supply source so that the duty-cycle of each fluid warming unit is accomplished during the work cycle.

* * * * *